United States Patent
Bilello et al.

(10) Patent No.: US 8,440,418 B2
(45) Date of Patent: May 14, 2013

(54) METABOLIC SYNDROME AND HPA AXIS BIOMARKERS FOR MAJOR DEPRESSIVE DISORDER

(75) Inventors: John Bilello, Durham, NC (US); Bo Pi, Carlsbad, CA (US)

(73) Assignee: Ridge Diagnostics, Inc., La Jolla, CA (US)

( * ) Notice: Subject to any disclaimer, the term of this patent is extended or adjusted under 35 U.S.C. 154(b) by 0 days.

(21) Appl. No.: 12/620,831

(22) Filed: Nov. 18, 2009

(65) Prior Publication Data

US 2010/0136700 A1 Jun. 3, 2010

Related U.S. Application Data

(60) Provisional application No. 61/115,710, filed on Nov. 18, 2008.

(51) Int. Cl.
*G01N 33/53* (2006.01)
*G01N 33/537* (2006.01)
*G01N 33/567* (2006.01)
*G01N 33/566* (2006.01)

(52) U.S. Cl.
USPC .......... 435/7.92; 435/7.1; 435/7.21; 435/7.8; 436/501; 436/503

(58) Field of Classification Search .................. None
See application file for complete search history.

(56) References Cited

U.S. PATENT DOCUMENTS

| | | | |
|---|---|---|---|
| 5,647,030 | A | 7/1997 | Jorgenson et al. |
| 5,658,802 | A | 8/1997 | Hayes et al. |
| 5,804,453 | A | 9/1998 | Chen |
| 5,882,203 | A | 3/1999 | Correa et al. |
| 7,041,206 | B2 | 5/2006 | Gephart et al. |
| 7,094,595 | B2 | 8/2006 | Cunningham et al. |
| 7,136,518 | B2 | 11/2006 | Griffin et al. |
| 7,418,290 | B2 | 8/2008 | Devlin et al. |
| 7,651,836 | B2 | 1/2010 | Matute Almau et al. |
| 8,158,374 | B1 | 4/2012 | He et al. |
| 2001/0045355 | A1 | 11/2001 | Gephart et al. |
| 2002/0095073 | A1 | 7/2002 | Jacobs et al. |
| 2003/0016360 | A1 | 1/2003 | Chase et al. |
| 2003/0032773 | A1 | 2/2003 | Herath et al. |
| 2003/0109420 | A1 | 6/2003 | Valkirs et al. |
| 2004/0110938 | A1 | 6/2004 | Parekh et al. |
| 2004/0117212 | A1 | 6/2004 | Kong et al. |
| 2004/0122790 | A1 | 6/2004 | Walker et al. |
| 2004/0152107 | A1 | 8/2004 | Altar et al. |
| 2004/0228765 | A1 | 11/2004 | Witty et al. |
| 2004/0228766 | A1 | 11/2004 | Witty et al. |
| 2005/0069936 | A1 | 3/2005 | Diamond et al. |
| 2005/0084880 | A1 | 4/2005 | Duman et al. |
| 2005/0095646 | A1 | 5/2005 | Sherman |
| 2005/0191694 | A1 | 9/2005 | Jacobs et al. |
| 2005/0239110 | A1 | 10/2005 | Rokutan et al. |
| 2005/0254062 | A1 | 11/2005 | Tan et al. |
| 2005/0254065 | A1 | 11/2005 | Stokowski |
| 2006/0019313 | A1 | 1/2006 | Andersson et al. |
| 2006/0063199 | A1 | 3/2006 | Elgebaly et al. |
| 2006/0154320 | A1 | 7/2006 | Zuk et al. |
| 2007/0054282 | A1 | 3/2007 | Liew |
| 2007/0059204 | A1 | 3/2007 | Witty et al. |
| 2007/0092888 | A1 | 4/2007 | Diamond et al. |
| 2007/0161042 | A1 | 7/2007 | Zuk et al. |
| 2008/0015465 | A1 | 1/2008 | Scuderi |
| 2008/0199866 | A1 | 8/2008 | Akil et al. |
| 2008/0281531 | A1 | 11/2008 | Rokutan et al. |
| 2010/0100333 | A1 | 4/2010 | Pi et al. |
| 2010/0280562 | A1 | 11/2010 | Pi et al. |
| 2010/0280760 | A1 | 11/2010 | Pi et al. |
| 2011/0213219 | A1 | 9/2011 | Bilello et al. |
| 2011/0245092 | A1 | 10/2011 | Bilello et al. |
| 2011/0269633 | A1 | 11/2011 | Bilello et al. |
| 2012/0178118 | A1 | 7/2012 | Pi et al. |
| 2012/0289422 | A1 | 11/2012 | He et al. |

FOREIGN PATENT DOCUMENTS

| | | |
|---|---|---|
| EP | 1586657 | 10/2005 |
| EP | 2006680 | 12/2008 |
| JP | 2004/208547 | 7/2004 |
| KR | 2005-0050768 | 6/2005 |
| KR | 2005-0115436 | 12/2006 |
| WO | WO 2007/130831 | 11/2001 |
| WO | WO 02/057790 | 7/2002 |
| WO | WO 2005/017203 | 2/2005 |
| WO | WO 2006/060393 | 6/2006 |
| WO | 2007/058986 | 5/2007 |
| WO | 2007/067819 | 6/2007 |
| WO | WO 2007/094472 | 8/2007 |
| WO | 2009/111595 | 9/2009 |
| WO | 2009/114627 | 9/2009 |
| WO | WO 2010/045490 | 4/2010 |
| WO | WO 2010/118035 | 10/2010 |
| WO | WO 2011/094308 | 8/2011 |

OTHER PUBLICATIONS

U.S. Appl. No. 60/824,471, filed Sep. 5, 2006, He.
U.S. Appl. No. 60/910,217, filed Apr. 5, 2007, He.
Andreassen and Vestbo, "Chronic obstructive pulmonary disease as a systemic disease: an epidemiological perspective," *Eur. Respir. J.*, 2003, 22(Suppl. 46):2s-4s.
Anthonisen et al., "Hospitalizations and Mortality in the Lung Health Study," *Am. J. Respir. Crit. Care Med.*, 2002, 166:333-339.
Ashton et al., "In-patient workload in medical specialties: 2. Profiles of individual diagnoses from linked statistics," *Q. J. Med.*, 1995, 88:661-672.
Barańczyk-Kuźma et al., "Tricyclic antidepressants as inhibitors of brain glutathione-S-transferase," *Pol. Merk. Lek.*, 2001, 11:472-475 (includes English summary).
Berthold-Losleben et al., "The TNF-alpha system: functional aspects in depression, narcolepsy and phychopharmacology," *Curr. Neuropharmacol.*, 2002, 3:193-202.
Bluthé et al., "Central injection of interleukin-13 potentiates LPS-induced sickness behavior in rats," *Neuroreport*, 2001, 12(18):3979-3983.

(Continued)

Primary Examiner — Olga N Chernyshev
(74) Attorney, Agent, or Firm — Fish & Richardson P.C.

(57) ABSTRACT

Materials and methods for using combinations of metabolic syndrome and HPA axis biomarkers for monitoring major depressive disorder.

5 Claims, 10 Drawing Sheets

OTHER PUBLICATIONS

Camilli et al., "Death Certificate Reporting of Confirmed Airways Obstructive Disease," *Am. J. Epidemiol.*, 1991, 133(8):795-800.

Carpenter and Bunney, "Adrenal cortical activity in depressive illness," *Am. J. Psychiatry*, 1971, 128:31-40.

Carroll, "Pituitary-adrenal function in depression," *Lancet*, 1968, 1: 1373-1374.

Celli et al., "The Body-Mass Index, Airflow Obstruction, Dyspnea, and Exercise Capacity Index in Chronic Obstructive Pulmonary Disease," *N. Engl. J. Med.*, 2004, 350(10):1005-1012.

Donaldson et al., "Relationship between exacerbation frequency and lung function decline in chronic obstructive pulmonary disease," *Thorax*, 2002, 57:847-852.

Drew and Hen, "Adult Hippocampal Neurogenesis as Target for the Treatment of Depression," *CNS Neurol. Disord. Drug Targets*, 2007, 6:205-218.

Engström et al., "Occurrence and Prognostic Significance of Ventricular Arrhythmia is Related to Pulmonary Function. A Study From "Men Born in 1914," Malmö, Sweden," *Circulation*, 2001, 103:3086-3091.

Fujita et al., "Circulating alpha-2-macroglobulin levels and depression scores in patients who underwent abdominal cancer surgery," *J. Surgical Res.*, 2003, 114: 90-94.

Gil et al., "Serotonin transport is modulated differently by tetanus toxin and growth factors," *Neurochem. Int.*, 2003, 42:535-542.

Hole et al., "Impaired lung function and mortality risk in men and women: findings from the Renfrew and Paisley prospective population study," *Brit. Med. J.*, 1996, 313:711-715.

Hung et al., "Insulin sensitivity, proinflammatory markers and adiponectin in young males with different subtypes of depressive disorder," *Clin. Endocrinol.*, 2007, 67(5): 784-789.

Hurst et al., "Use of Plasma Biomarkers at Exacerbation of Chronic Obstructive Pulmonary Disease," *Am. J. Respir. Crit. Care Med.*, 2006, 174:867-874.

Karege et al., "Low brain-derived neurotrophic factor (BDNF) levels in serum of depressed patients probably results from lowered platelet BDNF release unrelated to platelet reactivity," 2005, *Biol. Psychiatry*, 57: 1068-1072.

Kim et al., "Low plasma BDNF is associated with suicidal behavior in major depression," *Prog. Neuro-psychopharmacol. Biol. Psychiatry*, 2007, 31:78-85.

Kinder et. al., "Depression and the metabolic syndrome in young adults: findings from the third national health and nutrition examination survey," *Psychosomatic Medicine*, 2004, 66: 316-322.

Kubota et al., "Interleukin-15 and interleukin-2 enhance non-REM sleep in rabbits," *Am. J. Physiol. Regul. Integr. Comp. Physiol.*, 2001, 281:R1004-R1012.

Lopez-Leon et al., "Meta-analyses of genetic studies on major depressive disorder," *Mol. Psychiatry*, 2008, 13(8): 772-785.

Luo et al., "RANTES Stimulates Inflammatory Cascades and Receptor Modulation in Murine Astrocytes," *Glia*, 2002, 39:19-30.

Maes et al., "Higher $\alpha_1$ -antitrypsin, haptoglobin, ceruloplasmin and lower retinol binding protein plasma levels during depression: Further evidence for the existence of an inflammatory response during that illness," *J. Affect. Disord.*, 1992, 24:183-192.

Maes, "Major depression and activation of the inflammatory response system," *Adv. Exp. Med. Biol.*, 1999, 461:25-46.

Mannino et al., "Low Lung Function and Incident Lung Cancer in the United States. Data From the First National Health and Nutrition Examination Survey Follow-up," *Arch. Intern. Med.*, 2003, 163:1475-1480.

Marano et al., "Increased Plasma Concentration of Brain-Derived Neurotrophic Factor With Electroconvulsive Therapy: A Pilot Study in Patients With Major Depression," *J. Clin. Psychiatry*, 2007, 68:512-517.

Marques-Deak et al., "Cytokine profiles in women with different subtypes of major depressive disorder," *J. Psychiatr. Res.*, 2007, 41:152-159.

Michaelson et al., "Interleukin-7 Is Trophic for Embryonic Neurons and is Expressed in Developing Brain," *Dev. Biol.*, 1996, 179:251-263.

Mischoulon and Fava, "Docosahexanoic acid and ω-3 fatty acids in depression," *Psychiatr. Clin. North Am.*, 2000, 23(4):785-794.

Nissen, "Proteolytic modification of $\beta_2$-microglobulin in human serum," *Danish Med. Bul.*, 1993, 40:56-64.

Notkins, "New Predictors of Disease," *Sci. Amer.*, 2007, 71:72-79.

O'Brien et al., "Plasma cytokine profiles in depressed patients who fail to respond to selective serotonin reuptake inhibitor therapy," *J. Psychiatr. Res.*, 2007, 41:326-331.

Panagiotakos et al., "Inflammation, coagulation, and depressive symptomatology in cardiovascular disease-free people; the ATTICA study," *Eur. Heart J.*, 2004, 25:492-499.

Pariante et al., "The HPA axis in major depression: classical theories and new developments," *Trends Neurosci.*, 2008, 31(9): 464-468.

Park et al., "Vagus nerve stimulation for depression: rationale, anatomical and physiological basis of efficacy and future prospects," Acta Neurochirurgica Supplementum, 2007, 97:407-416.

Paus and Barrett, "Transcranial magnetic stimulation (TMS) of the human frontal cortex: implications for repetitive TMS treatment of depression," *Journal of Psychiatry and Neuroscience*, 2004, 29(4):268-279.

Pauwels et al., "Global Strategy for the Diagnosis, Management, and Prevention of Chronic Obstructive Pulmonary Disease. NHLBI/WHO Global Initiative for Chronic Obstructive Lung Disease (GOLD) Workshop Summary," *Am. J. Respir. Crit. Care Med.*, 2001, 163:1256-1276.

Pavón et al., "Th2 cytokine response in Major Depressive Disorder patients before treatment," *J. Neuroimmunol.*, 2006, 172:156-165.

Pavon et al., "Th2 response in jajor depression patients without treatment," *Soc. For Neurosci.*, Abstract No. 829.1, 2 pages.

Pelsers and Glatz, "Detection of brain injury by fatty acid-binding proteins," *Clin. Chem. Lab. Med.*, 2005, 43(8):802-809.

Pinto-Plata et al., "Profiling serum biomarkers in patients with COPD: associations with clinical parameters," *Thorax*, 2007, 62:595-601.

Plotsky et al., "Psychoneuroendocrinology of depression. Hypothalamic-pituitary-adrenal axis," *Phychiatr. Clin. North Am.*, 1998, 21(2): 293-307.

Politi et al., "Elevated plasma N-terminal ProBNP levels in unmedicated patients with major depressive disorder," *Neurosci. Lett.*, 2007, 417:322-325.

Reichek et al., "Antibody responses to bacterial antigens during exacerbations of chronic bronchitis," *Am. Rev. Respir. Dis.*, 1970, 101:238-244.

Rothermundt et al., "Inflammatory markers in major depression and melancholia," *J. Affect. Disord.*, 2001, 63:93-102.

Schroeter et al., "Serum markers support disease-specific glial pathology in major depression," *J. Affect. Disord.*, 2008, 3(2-3): 271-280.

Seemungal et al., "Effect of Exacerbation on Quality of Life in Patients with Chronic Obstructive Pulmonary Disease," *Am. J. Respir. Crit. Care Med.*, 1998, 157:1418-1425.

Sekiyama et al., "A Stress-Induced, Superoxide-Mediated Caspase-1 Activation Pathway Causes Plasma IL-18 Upregulation," *Immunity*, 2005, 22:669-677.

Sin and Man, "Chronic Obstructive Pulmonary Disease as a Risk Factor for Cardiovascular Morbidity and Mortality," *Proc. Am. Thorac. Soc.*, 2005, 2:8-11.

Smith et al., "Haemophilus influenzae and haemophilus parainfluenzae in chronic obstructive pulmonary disease," *Lancet*, 1976, 1:1253-1255.

Soler-Cataluna et al., "Severe acute exacerbations and mortality in patients with chronic obstructive pulmonary disease," *Thorax* 2005, 60: 925-931.

Taylor, M. & Fink, M., *Melancholia: The Diagnosis, Pathophysiology, and Treatment of Depressive Illness*, pp. 91-92, Cambridge University Press (2006).

Tsai, "The possible role of tissue-type plasminogen activator and the plasminogen system in the pathogenesis of major depression," *Med. Hypotheses*, 2006, 66:319-322.

von Känel et al., "Effects of Psychological Stress and Psychiatric Disorders on Blood Coagulation and Fibrinolysis: A Biobehavioral Pathway to Coronary Artery Disease?" *Psychosom. Med.*, 2001, 63:531-544.

Wilkinson et al., "Respiratory Syncytial Virus, Airway Inflammation, and FEV$_1$ Decline in Patients with Chronic Obstructive Pulmonary Disease," *Am. J. Respir. Crit. Care Med.*, 2006, 173:871-876.

Yang et al., "Stress-related modulation of matrix metalloproteinase expression," *J. Neuroimmunol.*, 2002, 133:144-150.

Zimmermann-Ivol et al., "Fatty Acid Binding Protein as a Serum Marker for the Early Diagnosis of Stroke," *Mol. Cell. Proteomics*, 2004, 3:66-72.

Arato et al., "Elevated CSF CRF in suicide victims," *Biol. Psychiatry*, 1989, 25(3):355-359.

Bai et al., "Capn4 overexpression underlies tumor invasion and metastasis after liver transplantation for hepatocellular carcinoma," *Hepatology*, 2009, 49(2):460-470.

Bernstein and Hess, "Vagus nerve stimulation therapy for pharmacoresistant epilepsy: effect on health care utilization," *Epilepsy Behav.*, 2007, 10(1):134-137.

Berthold-Losleben and Himmerich, "The TNF-alpha system: functional aspects in depression, narcolepsy and psychopharmacology," *Curr. Neuropharmacol.*, 2008, 6(3):193-202.

Hamner and Diamond, "Plasma dopamine and norepinephrine correlations with psychomotor retardation, anxiety, and depression in non-psychotic depressed patients: a pilot study," *Psychiatry Res.*, 1996, 64:209-211.

Hashimoto et al., "Plasma neuropeptide Y in patients with major depressive disorder," *Neurosci. Lett.*, 1996, 216(1):57-60.

Hosoi et al., "Electrical stimulation of afferent vagus nerve induces IL-lbeta expression in the brain and activates HPA axis," *Am. J. Physiol. Regul. Integr. Comp. Physiol.*, 2000, 279(1):R141-147.

Ikeda et al., "Modulation of monoamine transporter expression and function by repetitive transcranial magnetic stimulation," *Biochem. Biophys. Res. Commun.*, 2005, 327(1):218-224.

Janicak et al., "Transcranial magnetic stimulation in the treatment of major depressive disorder: a comprehensive summary of safety experience from acute exposure, extended exposure, and during reintroduction treatment," *J. Clin. Psychiatry*, 2008, 69(2):222-232.

Karege et al., "Decreased serum brain-derived neurotrophic factor levels in major depressed patients" *Psychiatry Res.*, 2002, 109(2):143-148.

Keller et al., "Optimizing outcomes in depression: focus on antidepressant compliance," *Int. Clin. Psychopharmacol.*, 2002, 17:265-271.

Lambert et al., "Reduced brain norepinephrine and dopamine release in treatment-refractory depressive illness evidence in support of the catecholamine hypothesis of mood disorders," *Arch. Gen. Psychiatry*, 2000, 57:787-793.

Leo et al., "Association between enhanced soluble CD40 ligand and proinflammatory and prothrombotic states in major depressive disorder: Pilot observations on the effects of selective serotonin reuptake inhibitor therapy," *J. Clin. Psychiatry*, 2006, 67:1760-1766.

O'Keane et al., "Changes in hypothalamic-pituitary-adrenal axis measures after vagus nerve stimulation therapy in chronic depression," *Biol. Psychiatry*, 2005, 58(12):963-968.

Papakostas et al., "Assessment of a multi-assay, serum-based biological diagnostic test for major depressive disorder: a Pilot and Replication Study," *Mol. Psychiartry*, (2011) doi: 10.1038/mp.2011.166. [Epub ahead of print].

Pasco et al., "Leptin in depressed women: Cross-sectional and longitudinal data from an epidemiologic study," *J. Affect. Disord.*, 2008, 107:221-225.

Rauchenzauner et al., "Brain-type natriuretic peptide release and seizure activity during vagal nerve stimulation," *Epilepsia*, 2007, 48(2):397-399.

Renshaw et al., "Multinuclear magnetic resonance spectroscopy studies of brain purines in major depression," *Am. J. Psychiatry*, 2001, 158:2048-2055.

Sackeim et al., "Vagus nerve stimulation (VNS) for treatment-resistant depression: efficacy, side effects, and predictors of outcome," *Neuropsychopharmacology*, 2001, 25(5):713-728.

Schroeter et al., "Serum markers support disease-specific glial pathology in major depression," *J. Affect. Disord.*, 2008, 111: 271-280.

Thase and Demitrack, "Evaluating clinical significance of treatment outcomes in studies of resistant major depression," *Biol. Psych.*, 2008, 63(7s):138s.

Vaccarino et al., "Association of major depressive disorder with serum myeloperoxidase and other markers of inflammation: a twin study," *Biol. Psychiatry*, 2008, 64(6):476-483.

van Londen et al., "Plasma levels of arginine vasopressin elevated in patients with major depression," *Neuropsychopharm.*, 1997, 17:284-292.

Villordon et al., "Variation in randomly amplified DNA markers and storage root yield in 'Jewel' sweet potato clones," *J. Amer. Soc. Hort. Sci.*, 1995, 120(5):734-740.

European Search Report for Application No. 09828159.5, dated Jul. 18, 2012, 7 pages.

METABOLIC SYNDROME AND HPA AXIS BIOMARKERS FOR MAJOR DEPRESSIVE DISORDER

CROSS-REFERENCE TO RELATED APPLICATIONS

This application claims benefit of priority from U.S. Provisional Application Ser. No. 61/115,710, filed on Nov. 18, 2008.

TECHNICAL FIELD

This document relates to materials and methods for monitoring major depressive disorder.

BACKGROUND

Biobehavioral research can be a challenging scientific endeavor, as biological organisms display wide-ranging individual differences in physiology. Most clinical disorders do not arise due to a single biological change, but rather are the result of interactions between multiple factors. Thus, different individuals affected by the same clinical condition (e.g., depression) may present with a different range or extent of symptoms, depending on the specific changes within each individual.

SUMMARY

The development of psychotropic drugs has relied on the quantification of disease severity through psychopathological parameters (e.g., the Hamilton scale for depression). Subjective factors and lack of a proper definition inevitably influence such parameters. Similarly, diagnostic parameters for enrollment of psychiatric patients in phase II and phase III clinical studies are centered on the assessment of disease severity and specificity by measurement of symptomatological scales, and there are no validated biological correlates for disease trait and state that can help in patient selection. In spite of recent progress in molecular diagnostics, the potential information contained within the patient genotype on the likely phenotypic response to drug treatment has not been effectively captured, particularly in non-research settings.

The immune system has a complex and dynamic relationship with the nervous system, both in health and disease. The immune system surveys the central and peripheral nervous systems, and can be activated in response to foreign proteins, infectious agents, stress, and neoplasia. Conversely, the nervous system modulates immune system function both through the neuroendocrine axis and through vagus nerve efferents. The hypothalamic-pituitary-adrenal (HPA) hyperactivity hypothesis states that when this dynamic relationship is perturbed, it results in neuropsychiatric disorders such as depression. HPA axis activity is governed by secretion of corticotropin-releasing hormone (CRH or CRF) from the hypothalamus. CRH activates secretion of adrenocorticotropic hormone (ACTH) from the pituitary, and ACTH, in turn, stimulates secretion of glucocorticoids (cortisol in humans) from the adrenal glands. Release of cortisol into the circulation has a number of effects, including elevation of blood glucose. If the negative feedback of cortisol to the hypothalamus, pituitary and immune system is impaired, the HPA axis can be continually activated, and excess cortisol is released. Cortisol receptors become desensitized, leading to increased activity of the pro-inflammatory immune mediators and disturbances in neurotransmitter transmission.

The ability to determine disease status on an individual basis thus would be useful for accurate assessment of a subject's specific status. There is a need, however, for reliable methods of diagnosing or determining predisposition to clinical conditions, and of assessing a subject's disease status or response to treatment. This document is based in part on the identification of methods for determining diagnosis, prognosis, or predisposition to depressive disorders. The methods can include developing an algorithm that includes multiple parameters such as HPA axis and metabolic biomarkers, measuring the multiple parameters, and using the algorithm to determine a quantitative diagnostic score. In some embodiments, algorithms for application of multiple biomarkers from biological samples such as cells, serum, or plasma can be developed for patient stratification, identification of pharmacodynamic markers, and monitor the treatment outcome. As used herein, a "biomarker" is a characteristic that can be objectively measured and evaluated as an indicator of a normal biologic or pathogenic process or pharmacological response to a therapeutic intervention.

The approach described herein differs from some of the more traditional approaches to biomarkers in the construction of an algorithm versus analyzing single markers or groups of single markers. Algorithms can be used to derive a single value that reflects disease status, prognosis, or response to treatment. As described herein, highly multiplexed microarray-based immunological tools can be used to simultaneously measure of multiple parameters. An advantage of using such tools is that all results can be derived from the same sample and run under the same conditions at the same time. In addition to traditional multivariate and regression analysis, high-level pattern recognition approaches can be applied. A number of tools are available, including PHB's proprietary BIOMARKER HYPER-MAPPING™ (BHM) technology. Other clustering approaches such as hierarchical clustering, self-organizing maps, and supervised classification algorithms (e.g., support vector machines, k-nearest neighbors, and neural networks) also can be used. Both BIOMARKER HYPER-MAPPING™ technology and supervised classification algorithms are likely to be of substantial clinical use.

In one aspect, this document features a method for determining whether a human subject has depression, comprising (a) providing numerical values for a plurality of parameters predetermined to be relevant to depression, wherein the plurality of parameters comprises one or more hypothalamic-pituitary-adrenal (HPA) axis markers and one or more metabolic markers; (b) individually weighting each of the numerical values by a predetermined function, each function being specific to each parameter; (c) determining the sum of the weighted values; (d) determining the difference between the sum and a control value; and (e) if the difference is greater than a predetermined threshold, classifying the individual as having depression, or, if the difference is not different than the predetermined threshold, classifying the individual as not having depression. The depression can be associated with major depressive disorder (MDD).

An algorithm can be used to calculate an MDD score that can be used to support the diagnosis of MDD. The HPA axis markers can be selected from the group consisting adrenocorticotropic hormone, cortisol, epidermal growth factor, granulocyte colony stimulating factor, pancreatic polypeptide, vasopressin, and corticotrophin releasing hormone, and the metabolic markers are selected from the group consisting of acylation stimulating protein, adiponectin, apolipoprotein CIII, C-reactive protein, fatty acid binding protein, prolactin, resistin, insulin, testosterone, and thyroid stimulating hormone. The plurality of parameters can comprise clinical measurements relevant to metabolic syndrome (e.g., clinical measurements are selected from the group consisting of body mass index, fasting glucose levels, blood pressure, central obesity, high density lipoprotein, and triglycerides). The plurality of parameters can comprise the level of one or more catecholamines or catecholamine metabolites in urine, one or more inflammatory biomarkers, and/or one or more neurotrophic biomarkers.

In another aspect, this document features a method for monitoring treatment of an individual diagnosed with a depression disorder, comprising (a) using an algorithm to determine a first MDD disease score based on the levels of a plurality of analytes in a biological sample from the individual, wherein the plurality of analytes comprise one or more HPA axis biomarkers and one or more metabolic biomarkers; (b) using the algorithm to determine a second MDD disease score after treatment of the individual for the depression disorder; (c) comparing the score in step (a) to the score in step (b) and to a control MDD disease score, and classifying the treatment as being effective if the score in step (b) is closer than the score in step (a) to the control MDD score, or classifying the treatment as not being effective if the score in step (b) is not closer than the score in step (a) to the control MDD score. The second MDD disease score can be determined weeks or months after treatment. Steps (b) and (c) can be repeated over time to monitor the individual's response to treatment, the change in the individual's MDD status, or the progression of MDD in the individual. A subset of the plurality of analytes can be measured at time points prior to and after the initiation of treatment.

The method can further comprise including in the algorithm parameters comprising clinical measurements relevant to metabolic syndrome (e.g., clinical measurements selected from the group consisting of body mass index, fasting glucose levels, blood pressure, central obesity, high density lipoprotein, and triglycerides). The biological sample can be serum, plasma, or cerebrospinal fluid. The biomarkers can be nucleic acids and the biological sample can be comprised of cells or tissue. The plurality of analytes can comprise the level of one or more catecholamines or catecholamine metabolites in urine. The one or more metabolic biomarkers can comprise one or more thyroid hormones, or testosterone. The plurality of analytes can comprise one or more inflammatory biomarkers and/or one or more neurotrophic biomarkers. The method can further comprise adjusting the treatment of the individual if the score in step (b) is not closer than the score in step (a) to the control MDD score. The control MDD score can be an MDD score calculated for a normal individual or the average of MDD scores calculated for a plurality of normal individuals.

In still another aspect, this document features a method for determining whether an individual is likely to have depression, comprising (a) providing a biological sample from the individual; (b) measuring the level of an analyte in the biological sample, wherein the analyte is selected from the group consisting of apolipoprotein CIII, epidermal growth factor, prolactin, and resistin; (c) comparing the measured level with a control level of the analyte; and (d) if the level of the analyte is greater than the control level, classifying the individual as likely to have depression, or if the level of the analyte is not greater than the control level, classifying the individual as not likely to have depression. The biological sample can be, for example, a serum sample. The depression can be associated with MDD.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
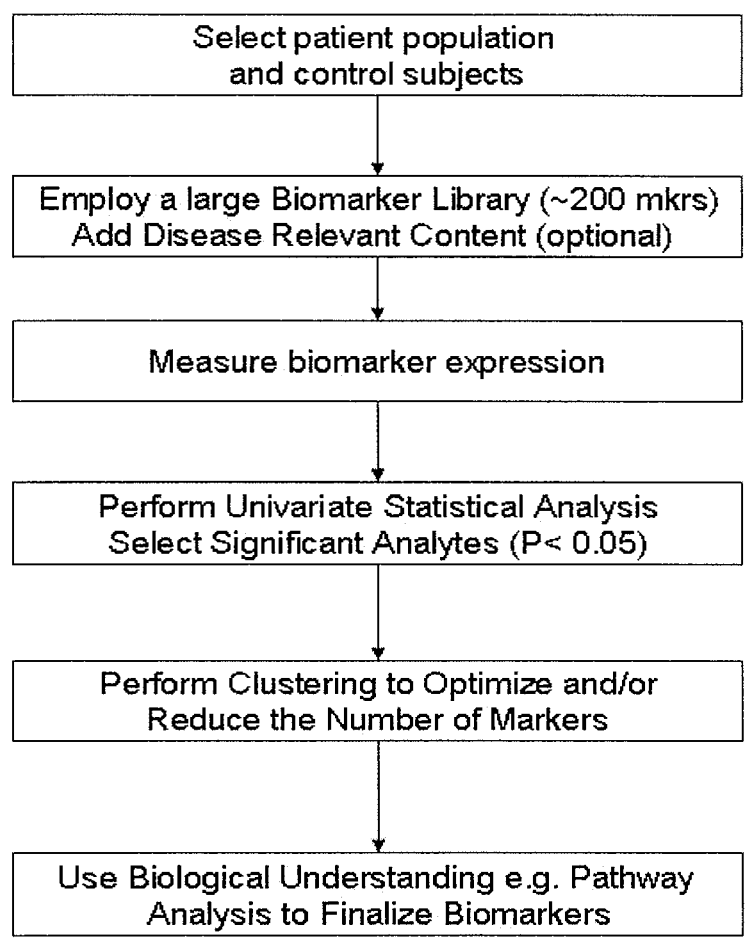
FIG. 1 is a flow diagram outlining the selection of biomarkers.

This document is based in part on the identification of methods for establishing a diagnosis, prognosis, or predisposition to depression disorder conditions by developing an algorithm, evaluating (e.g., measuring) multiple parameters, such as HPA axis and metabolic biomarkers, and using the algorithm to determine a set of quantitative diagnostic scores. Algorithms for application of multiple biomarkers from biological samples such as serum or plasma can be developed for patient stratification and identification of pharmacodynamic markers. The approach described herein differs from some of the more traditional approaches to biomarkers in the construction of an algorithm versus analyzing single markers or groups of single markers.

Algorithms

Algorithms for determining diagnosis, prognosis, status, or response to treatment, for example, can be determined for any clinical condition. The algorithms used in the methods provided herein can be mathematic functions containing multiple parameters that can be quantified using, for example, medical devices, clinical evaluation scores, or biological/chemical/physical tests of biological samples. Each mathematic function can be a weight-adjusted expression of the levels of parameters determined to be relevant to a selected clinical condition. The algorithms generally can be expressed in the format of Formula 1:

$$\text{Diagnostic score} = f(x1, x2, x3, x4, x5 \ldots xn) \quad (1)$$

The diagnostic score is a value that is the diagnostic or prognostic result, "f" is any mathematical function, "n" is any integer (e.g., an integer from 1 to 10,000), and x1, x2, x3, x4, x5 . . . xn are the "n" parameters that are, for example, measurements determined by medical devices, clinical evaluation scores, and/or tests results for biological samples (e.g., human biological samples such as blood, urine, or cerebrospinal fluid).

The parameters of an algorithm can be individually weighted. An example of such an algorithm is expressed in Formula 2:

$$\text{Diagnostic score} = a1*x1 + a2*x2 - a3*x3 + a4*x4 - a5*x5 \quad (2)$$

Here, x1, x2, x3, x4, and x5 can be measurements determined by medical devices, clinical evaluation scores, and/or test results for biological samples (e.g., human biological samples), and a1, a2, a3, a4, and a5 are weight-adjusted factors for x1, x2, x3, x4, and x5, respectively.

The diagnostic score can be used to quantitatively define a medical condition or disease, or the effect of a medical treatment. For example, an algorithm can be used to determine a diagnostic score for a disorder such as depression. In such an embodiment, the degree of depression can be defined based on Formula 1, with the following general formula:

$$\text{Depression diagnosis score} = f(x1, x2, x3, x4, x5 \ldots xn)$$

The depression diagnosis score is a quantitative number that can be used to measure the status or severity of depression in an individual, "f" is any mathematical function, "n" can be any integer (e.g., an integer from 1 to 10,000), and x1, x2, x3, x4, x5 . . . xn are, for example, the "n" parameters that are measurements determined using medical devices, clinical evaluation scores, and/or test results for biological samples (e.g., human biological samples).

In a more general format, multiple diagnostic scores Sm can be generated by applying multiple formulas to specific groupings of biomarker measurements, as illustrated in equation (3)

$$\text{Scores } Sm = fm(x1, \ldots xn) \quad (3)$$

Multiple scores can be useful, for example, in the identification of specific types of depression disorders and/or associated disorders. By way of example, it has been shown that a link exists between depressed mood and hypothyroidism, and it has been estimated that more than a third of people suffering from depression are hypothyroid. A biomarker panel including elements whose measurements may be indicative of hypothyroid function (e.g., anti-thyroid antibodies, T3, T4, TSH) can be used to calculate a score indicative of hypothyroidism. Combining these data with one or more panels indicative of MDD can allow a clinician to choose a regimen for treating both MDD and hypothyroidism. Cumulative experience based upon measurements with multiple biomarker panels and the success of treatment regimens can provide additional insight into the choice of a regimen.

For major depressive disorder and other mood disorders, treatment monitoring can help a clinician adjust treatment dose(s) and duration. An indication of a subset of alterations in individual biomarker levels that more closely resemble normal homeostasis can assist a clinician in assessing the efficacy of a regimen. Similarly, subclassification of a patient can be valuable in choosing an optimal drug or combination of drugs to use as a treatment regimen. Such changes, indicative of clinical efficacy, also can be useful to pharmaceutical companies during the development of new drugs.

To determine what parameters are useful for inclusion in a diagnostic algorithm, a biomarker library of analytes can be developed, and individual analytes from the library can be evaluated for inclusion in an algorithm for a particular clinical condition. In the initial phases of biomarker library development, the focus can be on broadly relevant clinical content, such as analytes indicative of inflammation, Th1 and Th2 immune responses, adhesion factors, and proteins involved in tissue remodeling (e.g., matrix metalloproteinases (MMPs) and tissue inhibitors of matrix metalloproteinases (TIMPs)). In some embodiments (e.g., during initial library development), a library can include a dozen or more markers, a hundred markers, or several hundred markers. For example, a biomarker library can include a few hundred protein analytes. As a biomarker library is built, new markers can be added (e.g., markers specific to individual disease states, and/or markers that are more generalized, such as growth factors). In some embodiments, analytes can be added to expand the library and to increase specificity beyond the inflammation, oncology, and neuropsychological foci by addition of disease related proteins obtained from discovery research (e.g., using differential display techniques, such as isotope coded affinity tags (ICAT) or mass spectroscopy).

The addition of a new protein analyte to a biomarker library can require a purified or recombinant molecule, as well as the appropriate antibody (or antibodies) to capture and detect the new analyte. Addition of a new nucleic acid-based analyte to a biomarker library can require the identification of a specific mRNA, as well as probes and detection systems to quantify the expression of that specific RNA. Although discovery of individual "new or novel" biomarkers is not necessary for developing useful algorithms, such markers can be included. Platform technologies that are suitable for multiple analyte detection methods as described herein typically are flexible and open to addition of new analytes.

While this document indicates that multiplexed detection systems can provide robust and reliable measurement of analytes relevant to diagnosing, treating, and monitoring clinical conditions: this does not preclude the use of assays capable of measuring the concentration of individual analytes from the panel (e.g., a series of single analyte ELISAs). The biomarker panels can be expanded and transferred to traditional protein arrays, multiplexed bead platforms or label-free arrays, and algorithms can be developed to support clinicians and clinical research.

Custom antibody array(s) can be designed, developed, and analytically validated for about 25-50 antigens. Initially, a panel of about 5 to 10 (e.g., 5, 6, 7, 8, 9, or 10) analytes can be chosen based on their ability to, for example, distinguish affected from unaffected subjects, or to distinguish between stages of disease in patients from a defined sample set. An enriched database, however, usually one in which more than 10 significant analytes are measured, can increase the sensitivity and specificity of test algorithms. Other panels can be run in addition to the panel reflecting HPA axis activity and metabolic syndrome, to further define the disease state or sub-classify patients. By way of example, data obtained from measurements of neurotrophic factors can discern patients with alterations in neuroplasticity. It is noted that such approaches also can include or be applied to other biological molecules including, without limitation, DNA and RNA.

Selection of Individual Parameters

In the construction of libraries or panels, the markers and parameters can be selected by any of a variety of methods. The primary driver for construction of a disease specific library or panel can be knowledge of a parameter's relevance to the disease. To construct a library for diabetes, for example, understanding of the disease would likely warrant the inclusion of blood glucose levels. Literature searches or experimentation also can be used to identify other parameters/markers for inclusion. In the case of diabetes, for example, a literature search might indicate the potential usefulness of hemoglobin A1c (HbAC), while specific knowledge or experimentation might lead to inclusion of the inflammatory markers tumor necrosis factor (TNF)-alpha receptor 2 (sTNF-RII), interleukin (IL)-6, and C-reactive protein (CRP), which have been shown to be elevated in subjects with type II diabetes.

The hypothalamic-pituitary-adrenal axis (also referred to as the HPA axis or HTPA axis) is a complex set of direct influences and feedback interactions between the hypothalamus, the pituitary gland, and the adrenal glands. The fine, homeostatic interactions between these three organs constitute the HPA axis, a major part of the neuroendocrine system that controls reactions to stress and regulates various body processes including digestion, the immune system, mood and sexuality, and energy usage. Hypercortisolemia has been observed in patients with major depression (see, e.g., Carpenter and Bunney (1971) *Am. J. Psychiatry* 128:31; Carroll (1968) *Lancet* 1:1373; and Plotsky et al. (1998) *Psychiatr. Clin. North Am.* 21:293-307). True hypercortisolemia and dysregulation of the HPA axis can be found in severe forms of depression, and elements of the HPA axis appear to be state rather than trait markers, in that they respond to external stimuli.

Metabolic biomarkers as defined herein refer to markers related to general health and regulation of metabolic processes, including energy metabolism. Among the possible metabolic markers that can be monitored are biomarkers related to metabolic syndrome, which is a combination of medical disorders that increase the risk of developing cardiovascular disease and diabetes. It has been suggested that depression may lead to development of cardiovascular disease through its association with metabolic syndrome. While little is known about the biochemical relationship between depression and metabolic syndrome, however, it was observed that women with a history of a major depressive episode were twice as likely to have the metabolic syndrome compared with those with no history of depression (Kinder et al. (2004) *Psychosomatic Medicine* 66:316-322).

FIG. 1 is a flow diagram detailing the first steps that can be included in development of a disease specific library or panel for use in determining a diagnosis or prognosis. The process can include two statistical approaches: 1) testing the distribution of biomarkers for association with the disease by univariate analysis; and 2) clustering the biomarkers into groups using a tool that divides the biomarkers into non-overlapping, uni-dimensional clusters, a process similar to principal component analysis. After the initial analysis, a subset of two or more biomarkers from each of the clusters can be identified to design a panel for further analyses. The selection typically is based on the statistical strength of the markers and current biological understanding of the disease.

Figure 2:
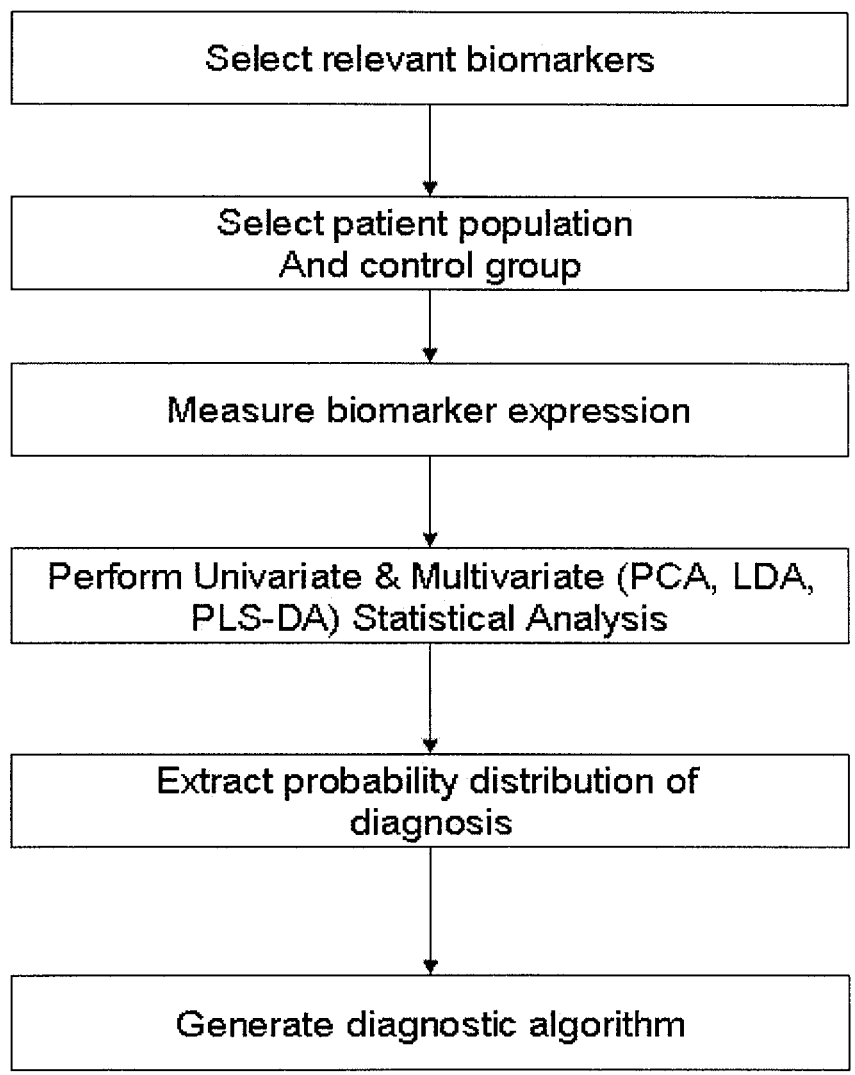
FIG. 2 is a flow diagram for the development of a disease specific library or panel with an algorithm for diagnostic development.

FIG. 2 is a flow diagram depicting steps that can be included to develop a disease specific library or panel for use in establishing diagnosis or prognosis. As shown in FIG. 2, the selection of relevant biomarkers need not be dependant upon the selection process described in FIG. 1, although the first process is efficient and can provide an experimentally and statistically based selection of markers. The process can be initiated, however, by a group of biomarkers selected entirely on the basis of hypothesis and currently available data. The selection of a relevant patient population and appropriately matched (e.g., for age, sex, race, BMI, and/or any other suitable parameters) population of normal subjects typically is involved in the process. In some embodiments, patient diagnoses can be made using state of the art methodology and, in some cases, by a single group of physicians with relevant experience with the patient population. Biomarker expression levels can be measured using Luminex MAP-x, Pierce SearchLight, the PHB MIMS instrument or any other suitable technology, including single assays (e.g., ELISA or PCR). Univariate and multivariate analyses can be performed using conventional statistical tools (e.g., not limited to: T-tests, principal components analysis (PCA), linear discriminant analysis (LDA), or Binary Logistic Regression).

Analyte Measurement

Any appropriate method(s) can be used to quantify the parameters included in a diagnostic/prognostic algorithm. For example, analyte measurements can be obtained using one or more medical devices or clinical evaluation scores to assess a subject's condition, or using tests of biological samples to determine the levels of particular analytes. As used herein, a "biological sample" is a sample that contains cells or cellular material, from which nucleic acids, polypeptides, or other analytes can be obtained. Examples of biological samples include, without limitation, urine, blood, serum, plasma, cerebrospinal fluid, pleural fluid, bronchial lavages, sputum, peritoneal fluid, bladder washings, secretions (e.g., breast secretions), oral washings, swabs (e.g., oral swabs), isolated cells, tissue samples, touch preps, and fine-needle aspirates.

Measurements can be obtained separately for individual parameters, or can be obtained simultaneously for a plurality of parameters. Any suitable platform can be used to obtain measurements for parameters. Useful platforms for simultaneously quantifying multiple parameters include, for example, those described in U.S. Provisional Application Nos. 60/910,217 and 60/824,471, U.S. Utility application Ser. No. 11/850,550, and PCT Publication No. WO2007/067819, all of which are incorporated herein by reference in their entirety.

An example of a useful platform utilizes MIMS label-free assay technology, which has been developed by Precision Human Biolaboratories, Inc. Briefly, local interference at the boundary of a thin film can be the basis for optical detection technologies. For biomolecular interaction analysis, glass chips with an interference layer of $SiO_2$ can be used as a sensor. Molecules binding at the surface of this layer increase the optical thickness of the interference film, which can be determined as set forth in U.S. Provisional Application Nos. 60/910,217 and 60/824,471, for example.

Figure 3:
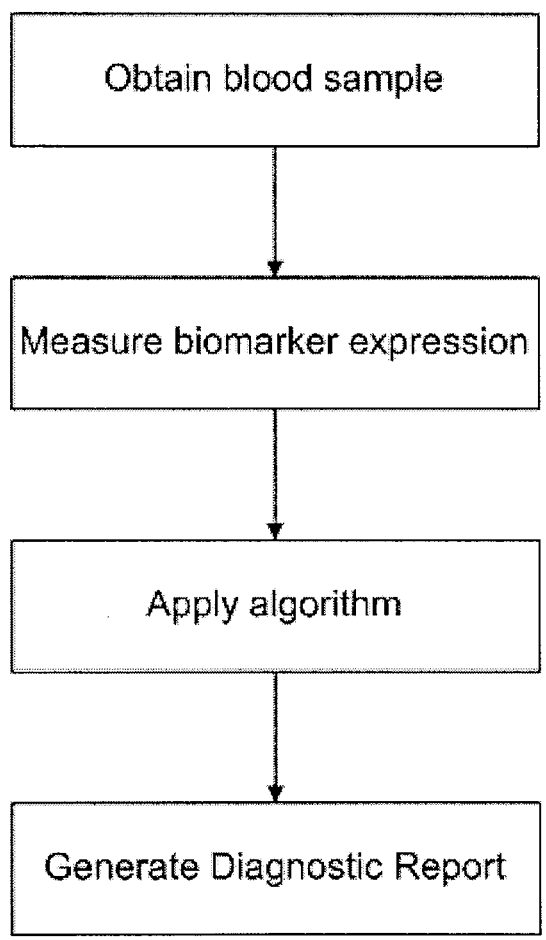
FIG. 3 is a flow diagram for development of a basic diagnostic score, where n diagnostic scores are generated. Diagnostic score $Sn=Fn(C1, \ldots Cn, M1, \ldots Mn)$, where Sn is the nth score and Fn is the nth function, and Cn and Mn are the nth coefficient and nth marker expression level, respectively.

FIG. 3 is a flow diagram depicting steps that can be included in establishing set scores for diagnostic development and application. The process can involve obtaining a biological sample (e.g., a blood sample) from a subject to be tested. Depending upon the type of analysis being performed, serum, plasma, or blood cells can be isolated by standard techniques. If the biological sample is to be tested immediately, the sample can be maintained at room temperature; otherwise the sample can be refrigerated or frozen (e.g., at −80° C.) prior to assay. Biomarker expression levels can be measured using a MIMS instrument or any other appropriate technology, including single assays such as ELISA or PCR, for example. Data for each marker can be collected, and an algorithm can be applied to generate a set diagnostic scores. The diagnostic scores, as well as the individual analyte levels, can be provided to a clinician for use in establishing a diagnosis and/or a treatment action for the subject.

Figure 4:
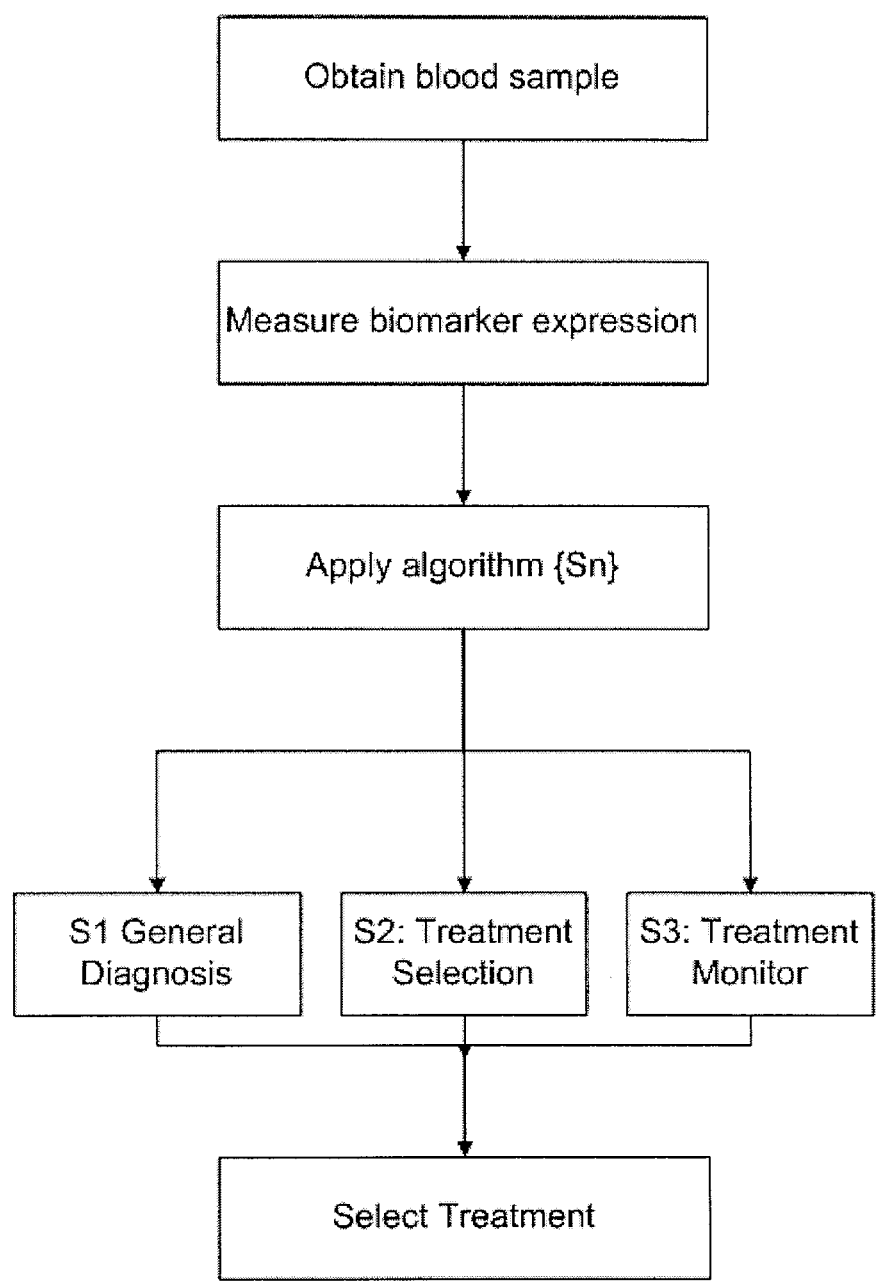
FIG. 4 is a flow diagram for the process of using blood to diagnose, select treatment, monitor treatment efficacy and optimize therapy. Diagnostic score $Sn=Fn(C1, \ldots Cn, M1, \ldots Mn)$, where Sn is the nth score and Fn is the nth function, and Cn and Mn are the nth coefficient and nth marker expression level, respectively.

FIG. 4 is a flow diagram of the process of using diagnostic scores to aid in determining a diagnosis, selecting treatments, and monitoring the treatment process. One or more multiple diagnostic scores can be generated from the expression levels of a set of biomarkers. In this example, multiple biomarkers can be measured from a patient blood sample; three diagnostic scores are generated by the algorithm. In some cases, a single diagnostic score can be sufficient to aid in making a diagnosis and selecting treatment. When the treatment regimen is selected and treatment starts, the patient can be monitored periodically by drawing their blood, measuring the biomarker levels and generating diagnostic scores. Multiple measurements can be used to develop S3. These multiple scores can be used to continually adjust the treatment (dose and schedule) and to periodically assess the patient's status, optimize and select new single or multiple agent therapeutics.

An example of platform useful for multiplexing is the FDA approved flow-based Luminex assay system (xMAP; World Wide Web at luminexcorp.com). This multiplex technology uses flow cytometry to detect antibody/peptide/oligonucleotide or receptor tagged and labeled microspheres. Since the system is open in architecture, Luminex can be readily adapted to host particular disease panels.

Diagnostic scores generated by the methods provided herein can be used to monitor treatment. For example, diagnostic scores and/or individual analyte levels can be provided to a clinician for use in establishing or altering a course of treatment for a subject. When a treatment is selected and treatment starts, the subject can be monitored periodically by collecting biological samples at two or more intervals, measuring biomarker levels to generate a diagnostic score corresponding to a given time interval, and comparing diagnostic scores over time. On the basis of these scores and any trends observed with respect to increasing, decreasing, or stabilizing diagnostic scores, a clinician, therapist, or other health-care professional may choose to continue treatment as is, to discontinue treatment, or to adjust the treatment plan with the goal of seeing improvement over time. For example, a decrease in disease severity as determined by a change in diagnostic score can correspond to a patient's positive response to treatment. An increase in disease severity as determined by a change in diagnostic score can indicate failure to respond positively to treatment and/or the need to reevaluate the current treatment plan. A static diagnostic score can correspond to stasis with respect to disease severity.

Diagnostic scores also can be used to stratify disease severity. In some cases, individual analyte levels and/or diagnostic scores determined by the algorithms provided herein can be provided to a clinician for use in diagnosing a subject as having mild, moderate, or severe depression. For example, diagnostic scores generated using the algorithms provided herein can be communicated by research technicians or other professionals who determine the diagnostic scores to clinicians, therapists, or other health-care professionals who will classify a subject as having a particular disease severity based on the particular score, or an increase or decrease in diagnostic score over a period of time. On the basis of these classifications, clinicians, therapists, or other health-care professionals can evaluate and recommend appropriate treatment options, educational programs, and/or other therapies with the goal of optimizing patient care. Diagnoses can be made, for example, using state of the art methodology, or can be made by a single physician or group of physicians with relevant experience with the patient population. When a patient is being monitored after treatment, movement between disease strata (i.e., mild, moderate, and severe depression) can indicate increasing or decreasing disease severity. In some cases, movement between disease strata can correspond to efficacy of the treatment plan selected for a particular subject or group of subjects.

After a patient's diagnostic scores are reported, a health-care professional can take one or more actions that can affect patient care. For example, a health-care professional can record the diagnostic score in a patient's medical record. In some cases, a health-care professional can record a diagnosis of MDD, or otherwise transform the patient's medical record, to reflect the patient's medical condition. In some cases, a health-care professional can review and evaluate a patient's medical record, and can assess multiple treatment strategies for clinical intervention of a patient's condition.

A health-care professional can initiate or modify treatment for MDD symptoms after receiving information regarding a patient's diagnostic score. In some cases, previous reports of diagnostic scores and/or individual analyte levels can be compared with recently communicated diagnostic scores and/or disease states. On the basis of such comparison, a health-care profession may recommend a change in therapy. In some cases, a health-care professional can enroll a patient in a clinical trial for novel therapeutic intervention of MDD symptoms. In some cases, a health-care professional can elect waiting to begin therapy until the patient's symptoms require clinical intervention.

A health-care professional can communicate diagnostic scores and/or individual analyte levels to a patient or a patient's family. In some cases, a health-care professional can provide a patient and/or a patient's family with information regarding MDD, including treatment options, prognosis, and referrals to specialists, e.g., neurologists and/or counselors. In some cases, a health-care professional can provide a copy of a patient's medical records to communicate diagnostic scores and/or disease states to a specialist.

A research professional can apply information regarding a subject's diagnostic scores and/or disease states to advance MDD research. For example, a researcher can compile data on MDD diagnostic scores with information regarding the efficacy of a drug for treatment of MDD symptoms to identify an effective treatment. In some cases, a research professional can obtain a subject's diagnostic scores and/or individual analyte levels to evaluate a subject's enrollment or continued participation in a research study or clinical trial. A research professional can classify the severity of a subject's condition based on the subject's current or previous diagnostic scores. In some cases, a research professional can communicate a subject's diagnostic scores and/or individual analyte levels to a health-care professional, and/or can refer a subject to a health-care professional for clinical assessment of MDD and treatment of MDD symptoms.

Any appropriate method can be used to communicate information to another person (e.g., a professional), and information can be communicated directly or indirectly. For example, a laboratory technician can input diagnostic scores and/or individual analyte levels into a computer-based record. In some cases, information can be communicated by making a physical alteration to medical or research records. For example, a medical professional can make a permanent notation or flag a medical record for communicating a diagnosis to other health-care professionals reviewing the record. Any type of communication can be used (e.g., mail, e-mail, telephone, and face-to-face interactions). Information also can be communicated to a professional by making that information electronically available to the professional. For example, information can be placed on a computer database such that a health-care professional can access the information. In addition, information can be communicated to a hospital, clinic, or research facility serving as an agent for the professional.

In some embodiments, a diagnosis of MDD, stratification of MDD severity, and/or treatment monitoring for MDD can be made based on the level of a single analyte. For example, apolipoprotein CIII levels can be measured in a biological sample from a subject and the level can be compared to a control level of apolipoprotein CIII. If the level measured in the subject is greater than the control level (e.g., 5%, 10%, 20%, 25%, 50%, 75%, 100%, or more than 100% greater than the control level), the subject can be classified as having, or being likely to have, MDD. If the level measured in the subject is not greater than the control level, the subject can be classified as not having, or not being likely to have, MDD. The severity of MDD also can be stratified based on the level of a single analyte in the subject, and MDD treatment can be monitored in the subject based on changes in the levels of one or more single analytes. For example, a diagnosis of MDD, stratification of MDD severity, or treatment monitoring for MDD can be made based on the measured level of a single analyte such as epidermal growth factor, prolactin, resistin, or apolipoprotein CIII, or combinations of two, three, or all of those four analytes. It is to be noted that, as for diagnostic scores, a health care or research professional can take one or more actions that can affect patient care based on the measured level of a single analyte (e.g., epidermal growth factor, prolactin, resistin, or apolipoprotein CIII).

The invention will be further described in the following examples, which do not limit the scope of the invention described in the claims.

EXAMPLES

Example 1

Diagnostic Markers of Depression

Methods as described herein were used to develop an algorithm for determining depression scores that are useful to, for example, diagnose or determine predisposition to major depressive disorder (MDD), or evaluate response to antidepressive therapeutics. Multiplexed detection systems such as those described herein were used to phenotype molecular correlates of depression. Preliminary studies indicated the value in using multiplexed antibody arrays to develop a panel of biomarkers in populations with MDD. The availability of biological markers reflecting psychiatric state (e.g., the type of pathology, severity, likelihood of positive response to treatment, and vulnerability to relapse) can impact both the appropriate diagnosis and treatment of depression. This systematic, highly parallel, combinatorial approach was proposed to assemble "disease specific signatures" using algorithms as described herein. The algorithm can then be used to determine the status of individuals and patients previously diagnosed with MDD. Table 1 exemplifies an MDD disease-specific biomarker library—a collection of tests useful to quantify proteins expressed in human serum.

Table 1 lists a series of biomarkers that have been evaluated as individual biomarkers of MDD as well as members of a disease specific multi-analyte panel. Two statistical approaches can be used for biomarker assessment and algorithm development: (1) univariate analysis for testing the distribution of biomarkers for association with MDD; and (2) linear discriminant analysis (LDA) and binary logistic regression for algorithm construction.

Univariate analysis of individual analyte levels: Using the Students T test, serum levels of each of the analytes tested using Luminex multiplex technology were analyzed for comparison of depressed versus normal subjects. The level of significance was set at $p \leq 0.05$.

Table 2 lists the biomarker measurements and p values (determined by an independent T test) for a subset of markers related to the HPA axis and metabolism.

Table 3 includes a partial list of different groups of metabolic and HPA biomarker combinations that can be used to generate diagnostic scores. These groups, or combination of these groups, can be used to diagnose different subtypes of depression disorder, or select and monitor treatments. In addition, other markers also can be added to these groups to further classify patients and develop a series of optimal panels for patient stratification as well as for diagnosis and management of depression.

Table 4 indicates how subsets of a biomarker panel affect the overall predictability of the resulting panel when the number of markers was changed from a nine (9) marker panel to a three (3) marker panel. As is apparent from this table, removal of some markers from a panel had little effect on the percentage of correct predictions.

By adding and subtracting analytes and determining the resultant predictability, the panel is optimized. Depending upon the criteria set for predictability (e.g., the ability to properly diagnose vs. the ability to predict the efficacy of an intervention), clinically valuable information is generated.

TABLE 1

MDD Biomarker Library

| Gene Symbol | Biomarker Name | Cluster |
| --- | --- | --- |
| — | Cortisol | HPA axis |
| EGF | Epidermal Growth Factor | HPA axis |
| GCSF | Granulocyte Colony Stimulating Factor | HPA axis |
| PPY | Pancreatic Polypeptide | HPA axis |
| ACTH | Adrenocorticotropic hormone | HPA axis |
| AVP | Arginine Vasopressin | HPA axis |
| CRH | Corticotropin-releasing hormone | HPA axis |
| A1AT | Alpha 1 Antitrypsin | Inflammation |
| A2M | Alpha 2 Macroglobin | Inflammation |
| ApoC3 | Apolipoprotein CIII | Inflammation |
| CD40L | CD40 ligand | Inflammation |
| IL-6 | Interleukin 6 | Inflammation |
| IL-13 | Interleukin 13 | Inflammation |
| IL-18 | Interleukin 18 | Inflammation |
| IL-1ra | Interleukin 1 Receptor Antagonist | Inflammation |
| MPO | Myeloperoxidase | Inflammation |
| PAI-1 | Plasminogen activator inhibitor-1 | Inflammation |
| TNFA | Tumor Necrosis Factor A | Inflammation |
| ACRP30 | Adiponectin | Metabolic |
| ASP | Acylation Stimulating Protein | Metabolic |
| FABP | Fatty Acid Binding Protein | Metabolic |
| INS | Insulin | Metabolic |
| LEP | Leptin | Metabolic |
| PRL | Prolactin | Metabolic |
| RETN | Resistin | Metabolic |
| — | Testosterone | Metabolic |
| TSH | Thyroid Stimulating Hormone | Metabolic |
| BDNF | Brain-derived neurotrophic factor | Neurotrophic |

TABLE 1-continued

MDD Biomarker Library

| Gene Symbol | Biomarker Name | Cluster |
|---|---|---|
| S100B | S100B | Neurotrophic |
| NTF3 | Neurotrophin 3 | Neurotrophic |
| GDNF | Glial cell line derived neurotrophic factor | Neurotrophic |
| ARTN | Artemin | Neurotrophic |

TABLE 2

Serum Biomarker Levels in MDD and Normal subjects

| Biomarker | Cluster | MDD | Control | p value |
|---|---|---|---|---|
| Cortisol | HPA axis | 93.8 | 88.5 | 0.4 |
| Epidermal Growth Factor | HPA axis | 306.9 | 162.5 | 0.09 |
| Granulocyte Colony Stimulating Factor | HPA axis | 11.3 | 7.9 | 0.05 |
| Pancreatic Polypeptide | HPA axis | 120.9 | 75.8 | 0.1 |
| Adiponectin | Metabolic | 3.5 | 3 | 0.3 |
| Acylation Stimulating Protein | Metabolic | 16558 | 11542 | 0.03 |
| Fatty Acid Binding Protein | Metabolic | 0.75 | 0.7 | 0.8 |
| Insulin | Metabolic | 13.6 | 3.5 | 0.05 |
| Leptin | Metabolic | 6.3 | 3.8 | 0.2 |
| Prolactin | Metabolic | 1.34 | 0.5 | 0.04 |
| Resistin | Metabolic | 1.33 | 0.85 | 0.02 |
| Testosterone | Metabolic | 2.4 | 2.8 | 0.2 |
| Thyroid Stimulating Hormone | Metabolic | 2.5 | 2.3 | 0.5 |

TABLE 3

Partial List of Biomarker Combinations
(9 member Panels) Marker Combination

Cortisol, ACRP30, PPY, EGF, G-CSF, PRL, RETN, ASP, TSH
Cortisol, ACRP30, EGF, FABP, LEP, PRL, RETN, Testosterone, TSH
Cortisol, ACRP30, EGF, FABP, PPY, PRL, RETN, TSH, Testosterone
Cortisol, ACRP30, EGF, Insulin, PPY, PRL, RETN, TSH, Testosterone
Cortisol, ACRP30, G-CSF, INS, PPY, PRL, RETN, TSH, Testosterone
ASP, ACRP30, G-CSF, INS, PPY, PRL, RETN, TSH, Testosterone
ASP, Cortisol, G-CSF, INS, PPY, PRL, RETN, TSH, Testosterone

TABLE 4

Example of a Biomarker Combination
and the Predictability of Subsets

| Marker Combination | % Correct Prediction |
|---|---|
| A1AT, A2M, ApoC3, EGF, G-CSF, ICAM-1, PRL, RETN, TNFA | 91.7 |
| A1AT, A2M, ApoC3, EGF, G-CSF, ICAM-1, PRL, TNFA | 87.5 |
| A1AT, ApoC3, EGF, G-CSF, ICAM-1, PRL, TNFA | 89.6 |
| A1AT, ApoC3, EGF, ICAM-1, PRL, TNFA | 88.5 |
| A1AT, ApoC3, EGF, PRL, TNFA | 88.5 |
| ApoC3, EGF, PRL, TNFA | 88.5 |
| ApoC3, PRL, TNFA | 87.5 |

Individual biomarkers were evaluated in further studies. In particular, levels of apolipoprotein CIII, epidermal growth factor, prolactin, and resistin were measured in serum from 50 depressed patients and 20 age-matched normal controls. As shown in FIGS. 7-10, each of these markers was present at a higher concentration in depressed patients than normal controls.

Example 2

Depression Biomarkers that Change After Drug Therapy

The present state of the art for monitoring depression is based on periodic clinical interviews rather than biological testing. Placebo effects, poly-pharmacy and inaccuracy of patient reporting can make it difficult to monitor efficacy and determine appropriate treatment. As disclosed herein, a biomarker panel can be used to predict future clinical outcomes or suitable dose adjustments based on biomarker measurement. This establishes the correlation between changes in the biomarker and changes in drug exposure, measured as plasma concentration or dose. One of the challenges is to prospectively plan and properly implement the model and to determine which metrics of drug exposure and biomarker time course are able to predict clinical outcomes.

FIG. 4 is a flow diagram depicting a process for using diagnostic scores to aid in diagnosis, selecting treatments, and monitoring the treatment process. In this example, multiple biomarkers are measured from a patient blood sample at baseline and at time points after initiation of therapy. Since the biomarker pattern may be different for patients who are on antidepressants as opposed to cognitive, electroconvulsive, or behavioral therapy, changes in the diagnostic score toward that of normal patients are an indication of effective therapy. As the cumulative experience with therapies increases, specific biomarker panels and/or algorithms are derived to monitor therapy with specific antidepressants, etc.

Since patients on therapy with antidepressants can become resistant, patients are monitored periodically by drawing blood, measuring biomarker levels, and generating diagnostic scores. Such multiple measurements are used to continually adjust treatment (e.g., dose and schedule), to periodically assess the patient's status, and to optimize and select new single or multiple agent therapeutics. In identifying biomarkers that change after initiation of therapy, the optimal experimental design is a prospective clinical trial wherein drug naïve patients are monitored during the course of therapy. However, cross-sectional studies can be used to identify biomarkers that are up or down regulated during treatment. Some examples of MDD biomarkers that are potentially altered subsequent to antidepressant therapy are shown in Table 5. While this example focuses on the level of each protein in serum (or plasma), similar studies can be done on mRNA expression (e.g., in isolated lymphocytes from patients undergoing treatment).

TABLE 5

Biomarker values in MDD patients on antidepressant therapy vs. those not on therapy

| Biomarker Name | Cluster | MDD No Drug | MDD + Drug | Control |
|---|---|---|---|---|
| Cortisol | HPA axis | 91 | 96 | 88.5 |
| Epidermal Growth Factor | HPA axis | 220 | 365 | 162.5 |
| Granulocyte Colony Stimulating Factor | HPA axis | 12.3 | 10.2 | 7.9 |
| Pancreatic Polypeptide | HPA axis | 138 | 108 | 75.8 |
| Adiponectin | Metabolic | 3.7 | 3.3 | 3 |
| Acylation Stimulating Protein | Metabolic | 15343 | 17062 | 11542 |
| Fatty Acid Binding Protein | Metabolic | 4 | 0.8 | 0.7 |
| Insulin | Metabolic | 8.9 | 16.9 | 3.5 |
| Leptin | Metabolic | 3.4 | 7.6 | 3.8 |
| Prolactin | Metabolic | 0.96 | 1.57 | 0.5 |

TABLE 5-continued

Biomarker values in MDD patients on antidepressant therapy vs. those not on therapy

| Biomarker Name | Cluster | MDD No Drug | MDD + Drug | Control |
|---|---|---|---|---|
| Resistin | Metabolic | 1.24 | 1.41 | 0.85 |
| Testosterone | Metabolic | 2.31 | 2.47 | 2.8 |
| Thyroid Stimulating Hormone | Metabolic | 2.24 | 2.78 | 2.3 |

Figure 5:
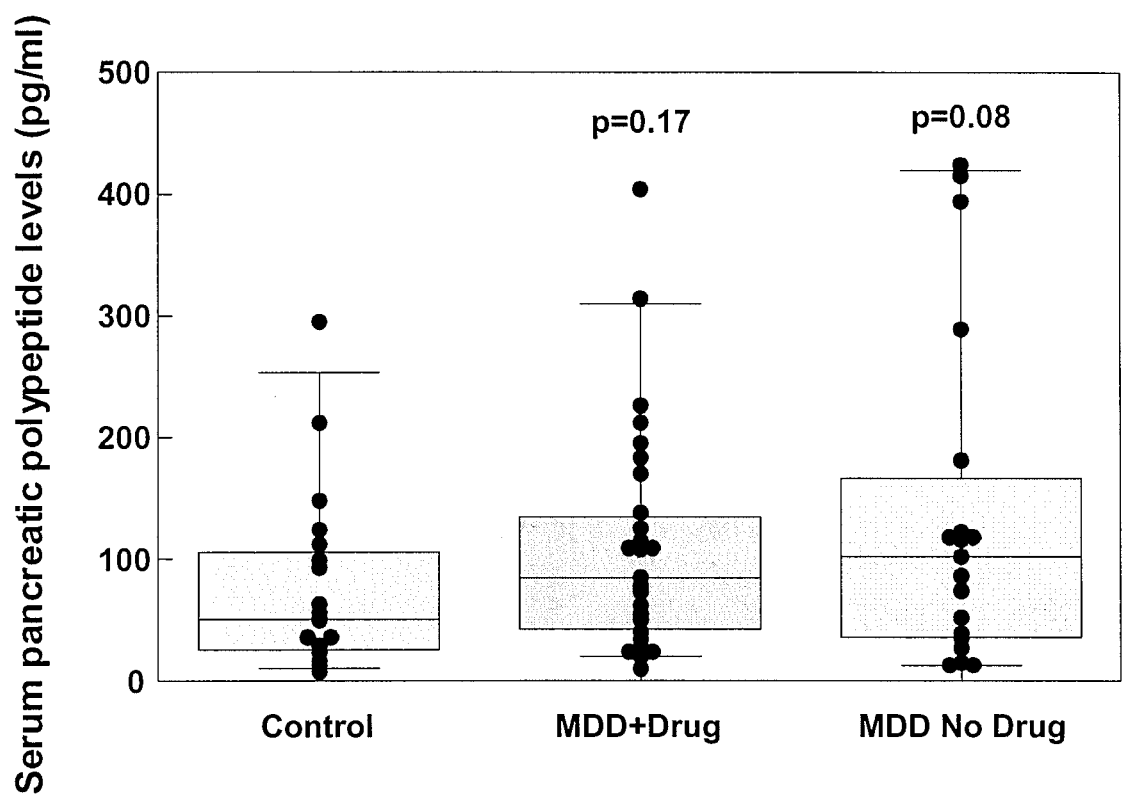
FIG. 5 is a box whisker plot indicating serum levels of pancreatic polypeptide in control and MDD patients, and MDD patients treated with antidepressants. The box represents the $25^{th}$-$75^{th}$ percentile. The line drawn within the box is the median concentration of the marker, and the whiskers are the $5^{th}$ and $95^{th}$ percentiles. Each dot represents an individual patient value.

An example of the raw data for a single biomarker (pancreatic polypeptide) is shown in FIG. 5. Each dot represents an individual subject. The boxes represent the $25^{th}$ through $75^{th}$ percentiles, while the whiskers indicate the $5^{th}$ and $95^{th}$ percentiles. In this case, it appeared that the mean values of serum pancreatic polypeptide in patients on antidepressants were similar to serum pancreatic polypeptide levels in normal subjects.

While this exercise suggests that serum levels of certain individual markers may change upon therapy, this was a cross-sectional study that did not take into account how therapy may affect individual patients.

Figure 6:
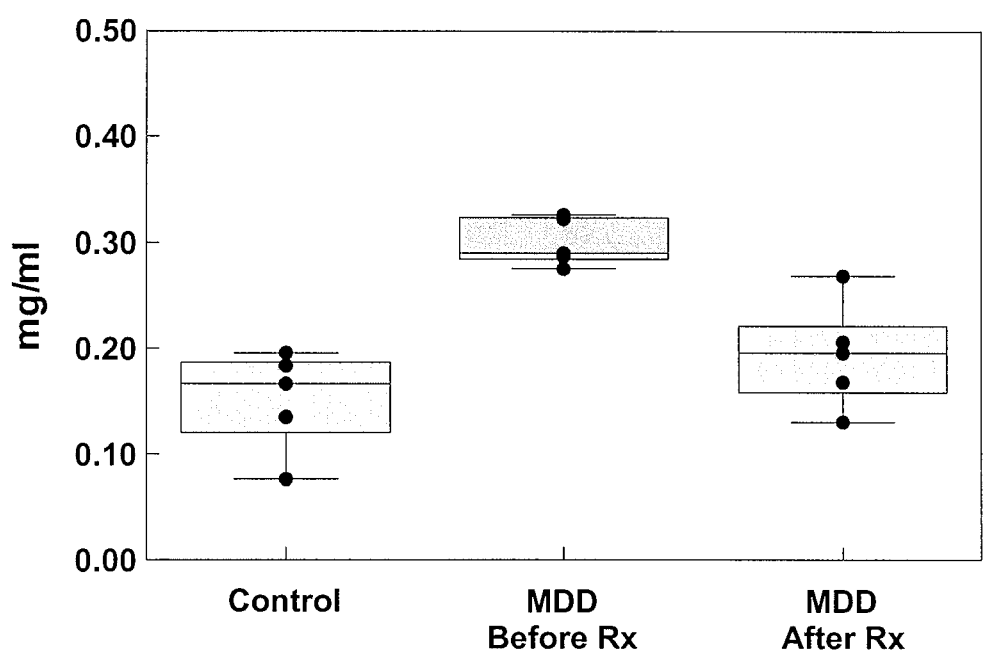
FIG. 6 is a box whisker plot indicating serum levels of hypothetical biomarker protein X in normal subjects and MDD patients before and after the initiation of treatment. Data are presented as in FIG. 5.
Figure 7:
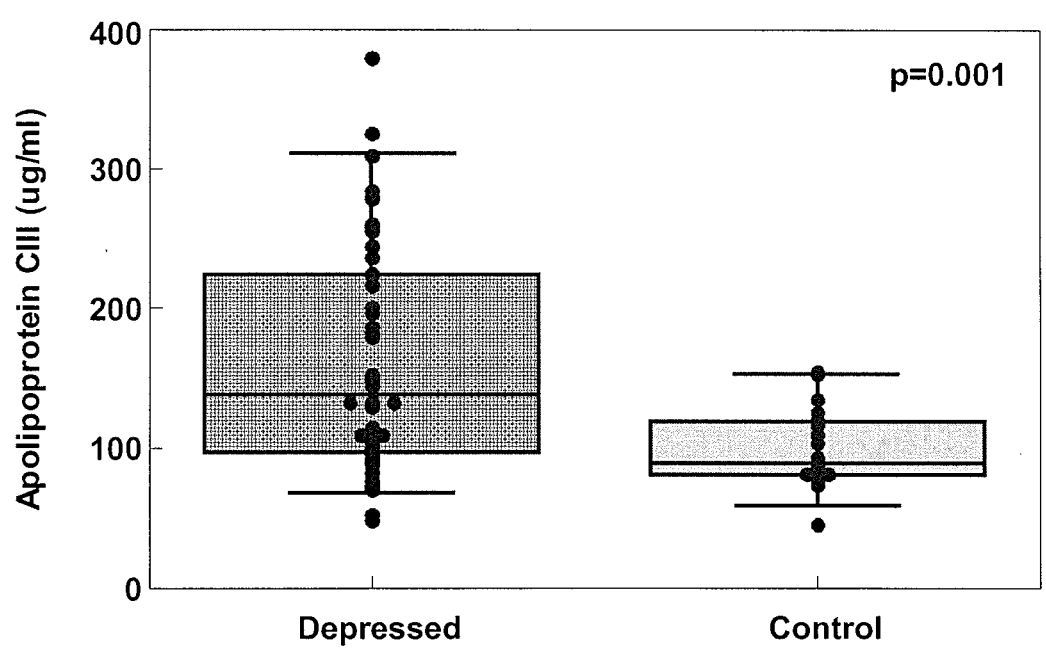
FIG. 7 is a box whisker plot of apolipoprotein CIII in serum samples from 50 depressed patients and 20 age-matched normal controls. Data are presented as in FIG. 5.
Figure 8:
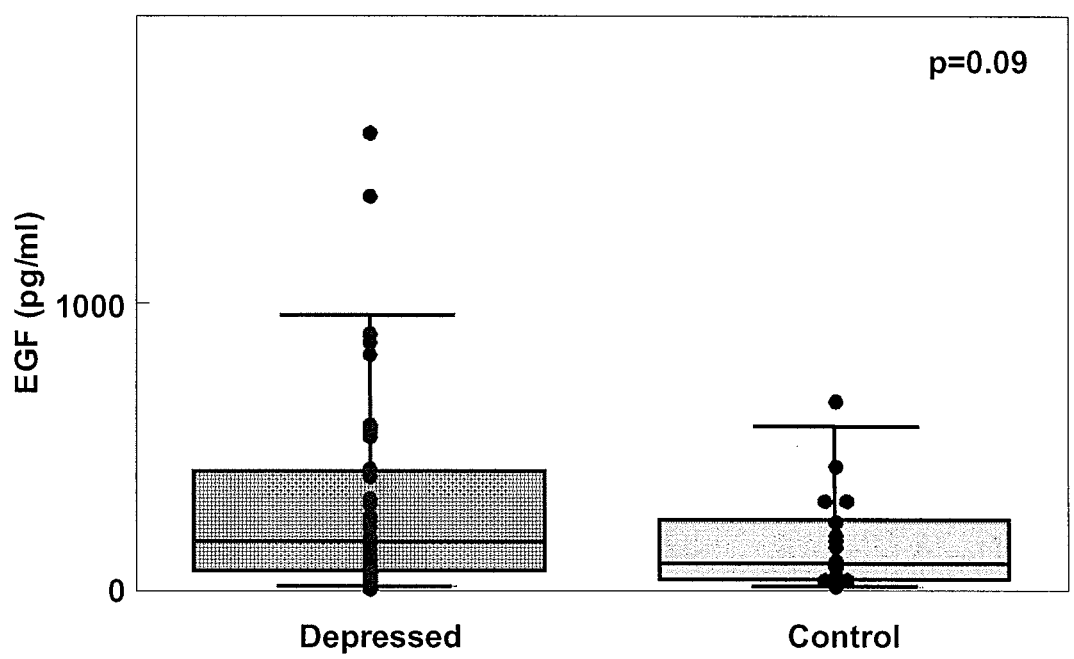
FIG. 8 is a box whisker plot of epidermal growth factor (EGF) in serum samples from 50 depressed patients and 20 age-matched normal controls. Data are presented as in FIG. 5.
Figure 9:
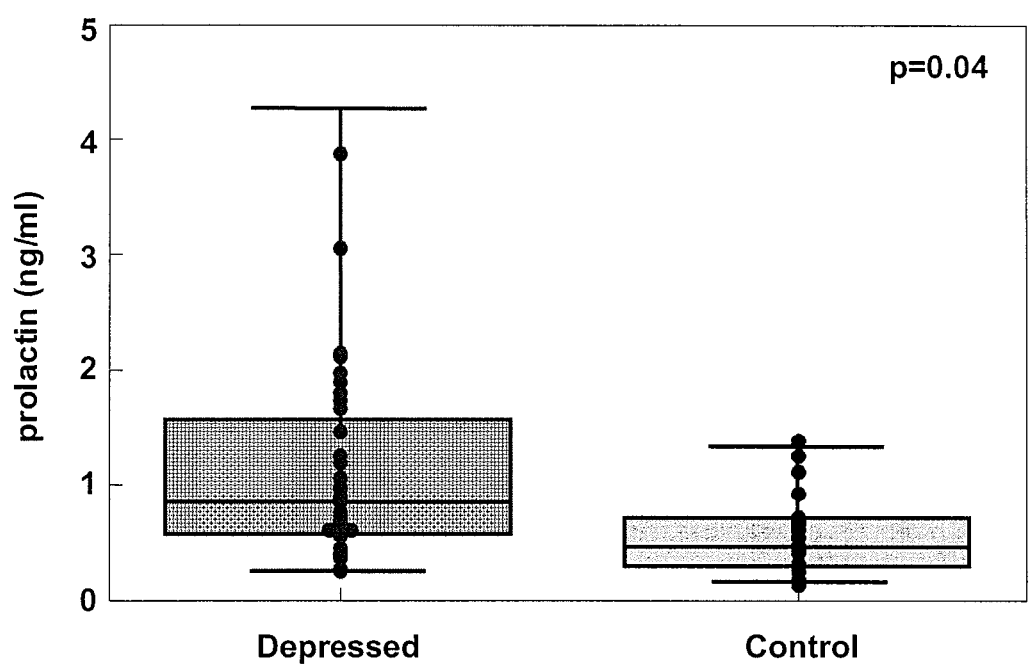
FIG. 9 is a box whisker plot of prolactin in serum samples from 50 depressed patients and 20 age-matched normal controls. Data are presented as in FIG. 5.
Figure 10:
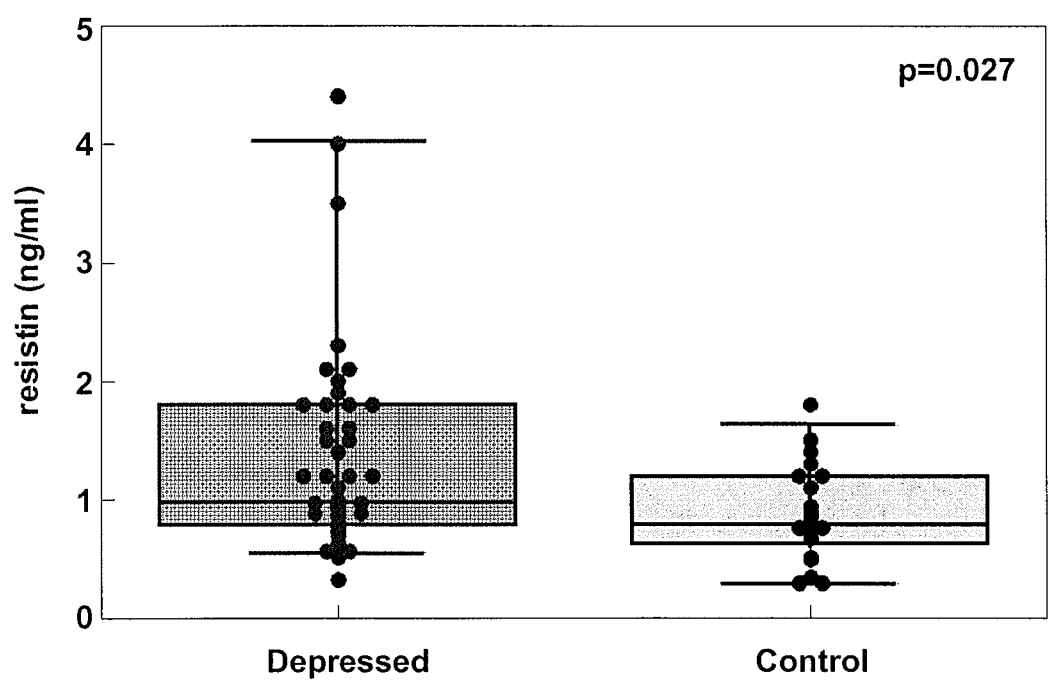
FIG. 10 is a box whisker plot of resistin in serum samples from 50 depressed patients and 20 age-matched normal controls. Data are presented as in FIG. 5.

It was proposed to monitor therapy by measuring groups of biomarkers at baseline and at time points after initiation of therapy. By way of example, FIG. 6 shows the distribution of blood levels of marker X in a hypothetical series of six MDD patients before and after treatment. The first point to be made from this graph is that the concentration of marker X is higher in untreated MDD patients as opposed to control subjects. Second, the levels of marker X in the MDD patients after treatment is similar to that of controls. The Student's t-Test is then used to compare two sets of data and to test the hypothesis that a difference in their means is significant. The difference in the means is of statistical significance on the basis of how many standard deviations that they are apart. The distance is judged significant using Student's t-statistic and its corresponding probability or significance that the absolute value of the t-statistic could be this large or larger by chance. In addition, the t-Test takes into account whether the populations are independent or paired. An Independent t-Test can be used when two groups are thought to have the same overall variance but different means. It can provide support for a statement about how a given population varies from some ideal measure, for example how a treated group compares with an independent control group. The independent t-Test can be performed on data sets with an unequal number of points. The paired test is executed only when two samples are of equivalent size (i.e., same number of points). It assumes that the variance for any point in one population is the same for the equivalent point in the second population. This test can be used to support conclusions about a treatment by comparing experimental results on a sample-by-sample basis. For example, this can be used to compare results for a single group before and after a treatment. This approach can help to evaluate two data sets whose means do not appear to be significantly different using the Independent t-Test. This test is performed only if the two data sets have an equal number of points. During the test(s), the Student's t-Statistic for measuring the significance of the difference of the means is calculated, and the probability (p-value) that the t-Statistic takes on its value by chance. The smaller the p-value, the more significant the difference in the means. For many biological systems, a level of significance of $p>0.05$ represents the probability that the t-Statistic is not achievable just by chance.

For example, application of the Student's t-Test to the data in FIG. 6, where there are equal number of points, showed that the difference in marker X expression between control subjects and patients with MDD was statistically significant (p=0.002), and the difference pre- and post-treatment also was significant (p=0.013). Lastly, there was no statistically significant difference between the control group and the MDD patients after treatment (p=0.35)

Such data can be used to obtain a frequency distribution of the data for the variable. This is done by identifying the lowest and highest values of the variable and then putting all the values of the variable in order from lowest to highest. The number of appearances of each value of the variable is a count of the frequency with which each value occurs in the data set. For example, if the MDD score is calculated using the algorithm, the patient population can be placed into groups having the same MDD score. If the 25 patients are monitored before and after treatment, one can establish what the frequency is for each MDD score and ascertain whether the treatment is effective. Table 6 presents an example of data in which the MDD scores were established at baseline and at week 4 post treatment (Rx). As can be seen, the number of patients with high scores (9 and 10) decreased from 13 to 6 after treatment, with a concomitant increase in the lower range of MDD scores (6 and 7) from 6 to 13, indicative of treatment efficacy.

TABLE 6

| MDD Score | # Pts before treatment | # Pts after treatment |
|---|---|---|
| 6 | 2 | 6 |
| 7 | 4 | 7 |
| 8 | 6 | 6 |
| 9 | 9 | 5 |
| 10 | 4 | 1 |

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A process for diagnosing a human subject as having a depression disorder, comprising:
    (a) performing an immunological assay to measure the level of each of EGF, resistin, and cortisol in a blood sample from the subject;
    (b) comparing the measured levels of EGF, resistin, and cortisol with control levels of EGF, resistin, and cortisol, respectively, in blood samples; and
    (c) diagnosing the subject as having said depression disorder when said measured levels of EGF, resistin, and cortisol are higher than said control levels.

2. The process of claim 1, wherein said depression disorder is major depressive disorder.

3. The process of claim 1, wherein said sample is a serum sample.

4. The process of claim 1, wherein said sample is a plasma sample.

5. The process of claim 1, wherein the control levels are levels of EGF, resistin, and cortisol in normal human subjects who do not have depression.

* * * * *